United States Patent
Hasegawa et al.

(10) Patent No.: US 7,564,951 B2
(45) Date of Patent: Jul. 21, 2009

(54) MULTILEAF COLLIMATOR

(75) Inventors: Yukihisa Hasegawa, Machida (JP); Minoru Awazu, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 12/053,879

(22) Filed: Mar. 24, 2008

(65) Prior Publication Data
US 2009/0080619 A1    Mar. 26, 2009

(30) Foreign Application Priority Data
Sep. 21, 2007    (JP) ............................. 2007-245730

(51) Int. Cl.
*G21K 1/04* (2006.01)
(52) U.S. Cl. ...................... 378/152; 378/149
(58) Field of Classification Search ......... 378/147–152; 250/363.1, 505.1
See application file for complete search history.

(56) References Cited

U.S. PATENT DOCUMENTS
2008/0205599 A1 *   8/2008   Hashimoto ................. 378/148

FOREIGN PATENT DOCUMENTS
JP    2001-129104 A    5/2001

\* cited by examiner

*Primary Examiner*—Jurie Yun
(74) *Attorney, Agent, or Firm*—Pearne & Gordon LLP

(57) ABSTRACT

A multileaf collimator includes a first leaf block group including plural leaf blocks, a second leaf block group including plural leaf blocks arranged in the same direction as the first leaf block group and disposed opposite the leaf blocks of the first leaf block group, plural magnetic layers located on the respective leaf blocks of the first and second leaf block groups so as to be positioned on faces of the leaf blocks along a moving direction of the leaf blocks, plural magnetic sensors mounted on the respective leaf blocks and varying output signals when the respective leaf blocks are moved in an oncoming direction or a departing direction, and a control device controlling drive mechanisms according to the output signals delivered by the respective magnetic sensors so that spacing between the leaf blocks of the first and second leaf blocks is adjusted into a target configuration.

8 Claims, 7 Drawing Sheets

MULTILEAF COLLIMATOR

CROSS-REFERENCE TO RELATED APPLICATIONS

This application is based upon and claims the benefit of priority from the prior Japanese Patent Application No. 2007-245730 filed on Sep. 21, 2007, the entire contents of which are incorporated herein by reference.

BACKGROUND OF THE INVENTION

1. Field of the Invention

The present invention relates to a multileaf collimator which adjusts radiation irradiated from a radiation generator toward a patient into a shape according to an affected part of the patient.

2. Description of the Related Art

One type of conventional multileaf collimator includes first and second groups disposed opposite to each other. Each group includes a plurality of leaf blocks arranged in a direction. The leaf blocks of the first group are oppositely disposed so as to be perpendicular to the leaf blocks of the second group The leaf blocks of the first group are connected to a drive mechanism having an electric motor serving as a drive source so that upon normal rotation of the motor, the leaf blocks of the first group are moved in such a direction that the leaf blocks of the first group are departed away from the leaf blocks of the second group. When the motor is reverse rotated, the leaf blocks of the first group are moved so as to come close to the leaf blocks of the second group. The leaf blocks of the second group are connected to a drive mechanism including an electric motor serving as a drive source. Upon normal rotation of the motor, the leaf blocks of the second group are moved so as to depart from the leaf blocks of the first group. On the other hand, the leaf blocks of the second group are moved close to the leaf blocks of the first group upon reverse rotation of the motor. The multileaf collimator includes detectors which detect current positions of the leaf blocks of the first and second groups respectively. Amounts of rotation of the motors are controlled based on the results of detection of current positions by the detectors respectively, whereby the spacing between the first and second leaf block groups is adjusted to a target configuration.

JP-A-2001-129104 discloses a multileaf collimator including a plurality of resistors serving as detectors and having different resistivity. The resistors are applied to a common leaf block so as to be arranged in a direction of movement of the leaf blocks. When the leaf blocks are moved in the oncoming or departing direction, the leaf blocks are moved while contacting paired electrodes. A voltage with a predetermined level is applied between the paired electrodes so that a current position of each leaf block is detected based on a magnitude of electric current flowing from one electrode to the other electrode. In the disclosed multileaf collimator, the resistance value varies according to variations in a mechanical contact resistance between the electrodes and the resistor. The resistance value also varies according to presence or absence of foreign matter such as dust. The resistance value further varies according to an external temperature. Accordingly, since current positions of the plural leaf blocks cannot be detected accurately, the spacing between the first and second leaf block groups cannot be set to a target configuration accurately.

SUMMARY OF THE INVENTION

Therefore, an advantage of the present invention is to provide a multileaf collimator in which the spacing between the first and second leaf block groups can be set to a target configuration accurately.

To achieve the advantage, one aspect of the present invention provides a multileaf collimator comprising a first leaf block group including a plurality of leaf blocks arranged in a direction, a second leaf block group including a plurality of leaf blocks arranged in the same direction as the first leaf block group, the leaf blocks of the second leaf block group being opposed to the leaf blocks of the first leaf block group in a direction orthogonal to the direction in which the leaf blocks of the first leaf block group are arranged, a plurality of drive mechanisms provided on the respective leaf blocks of the first and second leaf block groups, the drive mechanisms moving the leaf blocks of the first or second leaf block group in an oncoming direction in which the leaf blocks of the first or second leaf block group come close to the leaf blocks of the second or first leaf block or in a departing direction in which the leaf blocks of the first or second leaf block group depart from the leaf blocks of the second or first leaf block group, a plurality of magnetic layers which are provided on the respective leaf blocks of the first and second leaf block groups so as to be positioned on faces of the leaf blocks along a moving direction of the leaf blocks, each of the magnetic layers having a first magnetized part which is magnetized in a north pole and a second magnetized part which is magnetized in a south pole, a plurality of magnetic sensors which are provided on the respective leaf blocks of the first and second leaf block groups, the magnetic sensors being stationary in a noncontact state with respect to the respective leaf blocks, the magnetic sensors varying output signals when the respective leaf blocks are moved in the oncoming direction or the departing direction, and a control device which controls the drive mechanisms according to the output signals delivered by the respective magnetic sensors so that a space defined between the leaf blocks of the first and second leaf blocks is adjusted into a target configuration.

In the above-described construction, the magnetic layers are provided on the respective leaf blocks of the first and second leaf block groups so as to be positioned on the faces of the leaf blocks along a moving direction of the leaf blocks. Each magnetic layer has the first magnetized part which is magnetized in the north pole and the second magnetized part which is magnetized in the south pole. The magnetic sensors are disposed so as to be stationary in the noncontact state with respect to the magnetic layers. The drive mechanisms are controlled based on the output signals of the magnetic sensors. Consequently, the spacing between the first and second leaf block groups can be set to a target configuration accurately without being adversely affected by variations in the resistance values.

BRIEF DESCRIPTION OF THE DRAWINGS

Other objects, features and advantages of the present invention will become clear upon reviewing the following description of the embodiment with reference to the accompanying drawings, in which.

DETAILED DESCRIPTION OF THE INVENTION

Figure 1:
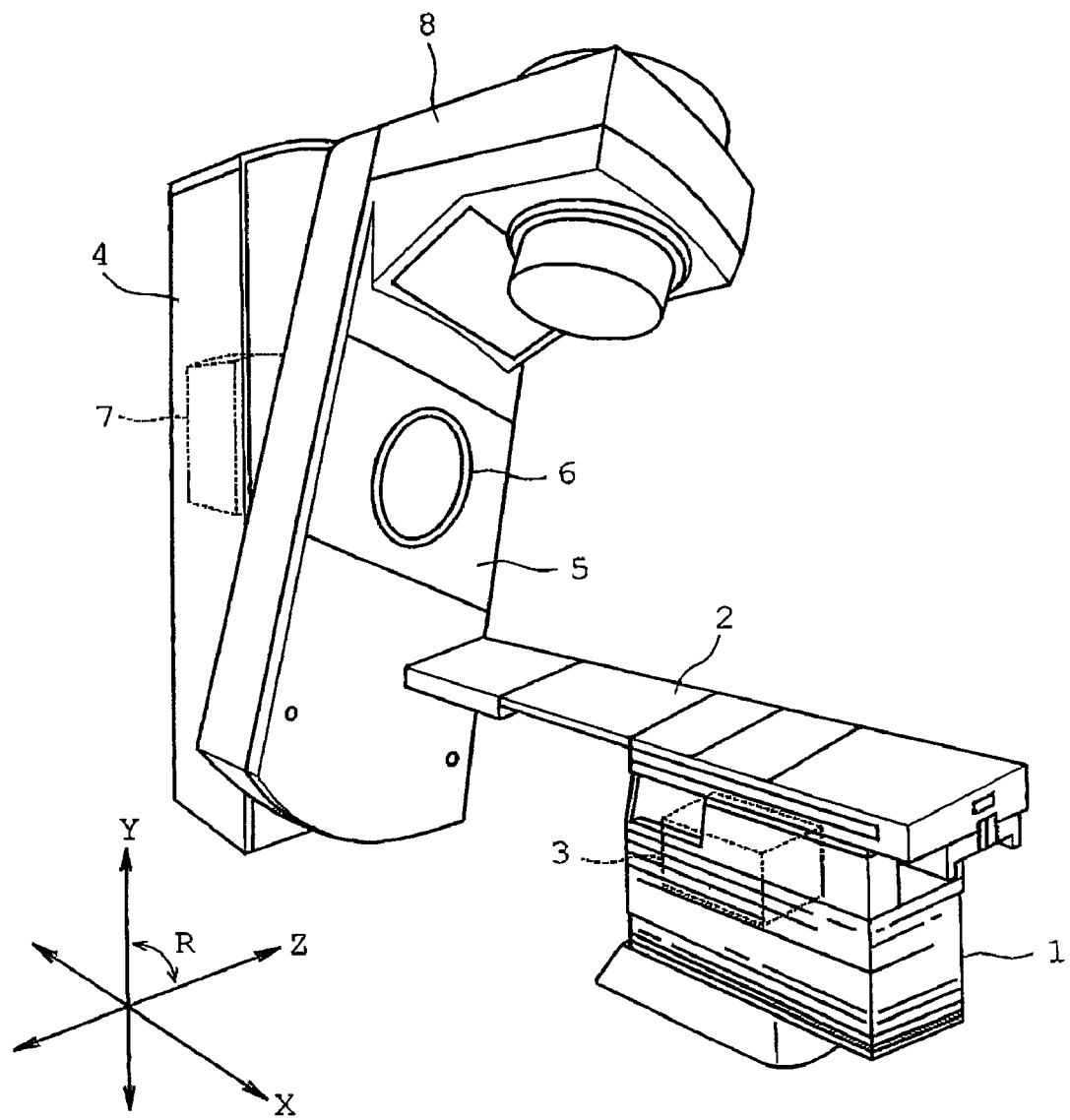
FIG. 1 is a perspective view of a radiation treatment machine of a first embodiment of the present invention.

A first embodiment of the present invention will be described with reference to FIGS. 1 to 6. Referring to FIG. 1, a radiation treatment machine or radiotherapy machine is shown to which the multileaf collimator of the invention is applied. The radiation treatment machine includes a stand 1 having an upper end on which a horizontal treatment table 2 extending in the X direction is mounted as shown in FIG. 1. A patient is to be put on the treatment table 2 so that the head and legs of the patient are directed in the X direction for the purpose of medical treatment. The treatment table 2 is connected to an XY drive mechanism including an X-direction motor and a Y-direction motor both serving as drive sources. The XY drive mechanism is housed in the stand 1. An amount of rotation of the X-direction motor is controlled so that the treatment table 2 is moved to a horizontal X-direction target position. An amount of rotation of the Y-direction motor is controlled so that the treatment table 2 is moved to a vertical Y-direction target position.

Figure 2:
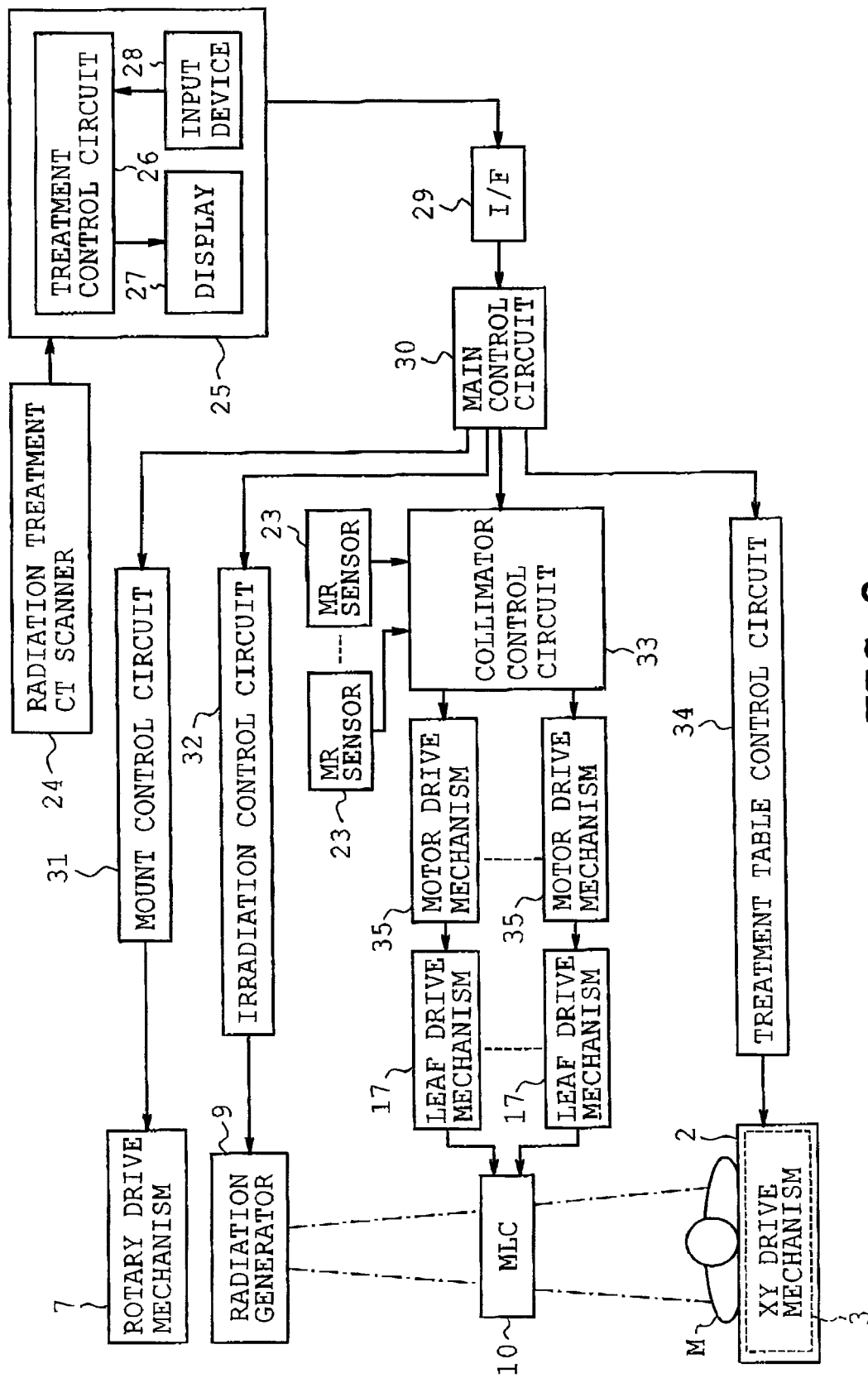
FIG. 2 is a block diagram showing an electrical arrangement of the radiation treatment machine.

A mount 5 is provided on a mount support 4 so as to be rotatable about a shaft 6 directed in the X direction as shown in FIG. 1. A rotary drive mechanism 7 is housed in the mount support 4, and the shaft 6 of the mount 5 is connected to the rotary drive mechanism 7. The rotary drive mechanism 7 includes an R-direction motor serving as a drive source. An amount of rotation of the R-direction motor is controlled so that the mount 5 is rotated about the shaft 6 to an R-direction target position. An irradiation head 8 is fixed to the mount 5. An X-radiation generator 9 is housed in the irradiation head 8 as shown in FIG. 2. The X-radiation generator 9 includes an acceleration section which accelerates electrons, a deflection section which deflects the accelerated electrons to the treatment table 2, and a target which applies the deflected electrons to a metal thereby to generate treatment X rays. A multileaf collimator 10 is housed in the irradiation head 8 so as to be located between the target and an X-ray outlet. The multileaf collimator adjusts an X-ray irradiation field on the body surface of a patient according to the shape of an affected part.

Figure 3:
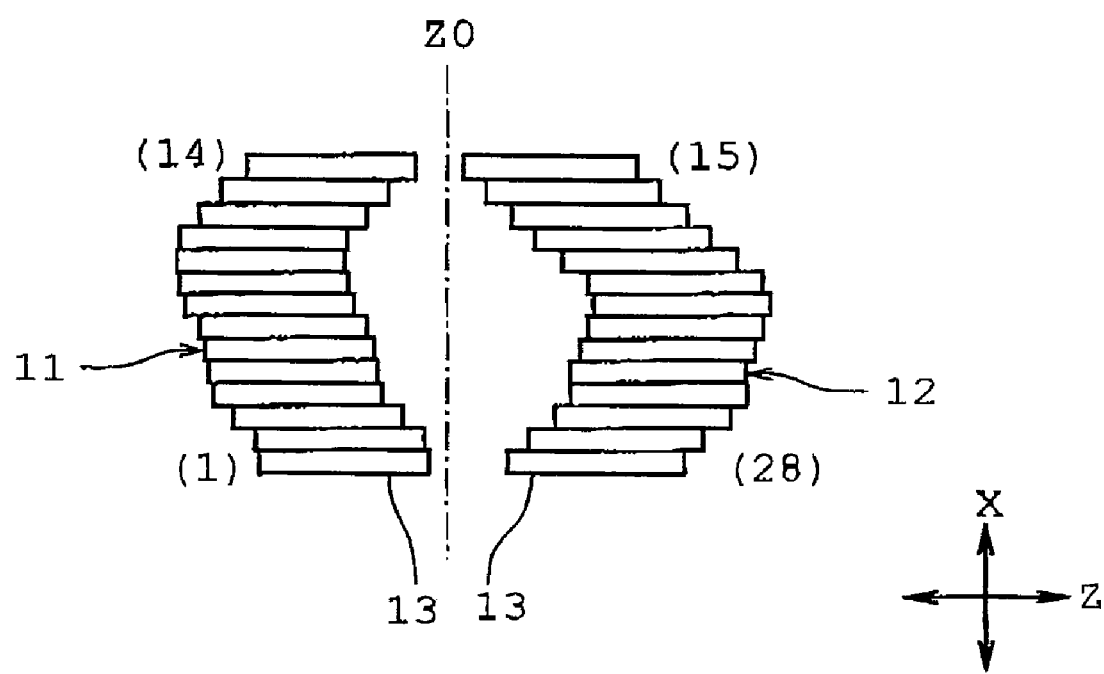
FIG. 3 shows a multileaf collimator as viewed from an X-ray irradiation axis.

The construction of the multileaf collimator will be described. The irradiation head 8 houses a first leaf block group 11 and a second leaf block group 12 both disposed so as to be spaced from each other in the Z direction as shown in FIG. 3. The Z direction and the X direction intersect at right angles in the same horizontal plane. Thus, the Z direction serves as an orthogonal direction. Each of the first and second leaf block groups 11 and 12 comprises a plurality of leaf blocks (14 leaf blocks, for example) aligned in a row in the X direction in the irradiation head 8. Leaf blocks 13 of the first leaf block group 11 are opposed to leaf blocks 13 of the second leaf block group in the Z direction. Each leaf block 13 is made from tungsten or lead that can cut off treatment X rays and formed into an arc-shaped plate having two flat and smooth arc-shaped faces 14 and 15 and two flat and smooth faces 16. The arc-shaped faces 14 and 15 of the leaf blocks 13 are concentric with each other. A common center CP (see FIG. 5) of the arc-shaped faces 14 and 15 is set on a target which is an irradiation source of X rays. The X rays serve as treatment X rays and the target serves as the irradiation source.

Figure 4B:
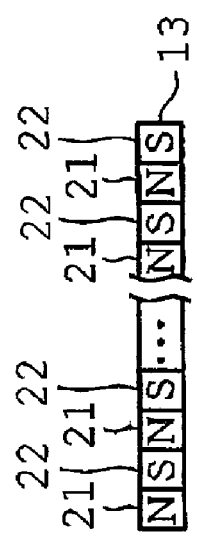
FIG. 4B shows the leaf block as viewed from arrow 4B in FIG. 4A.
Figure 4A:
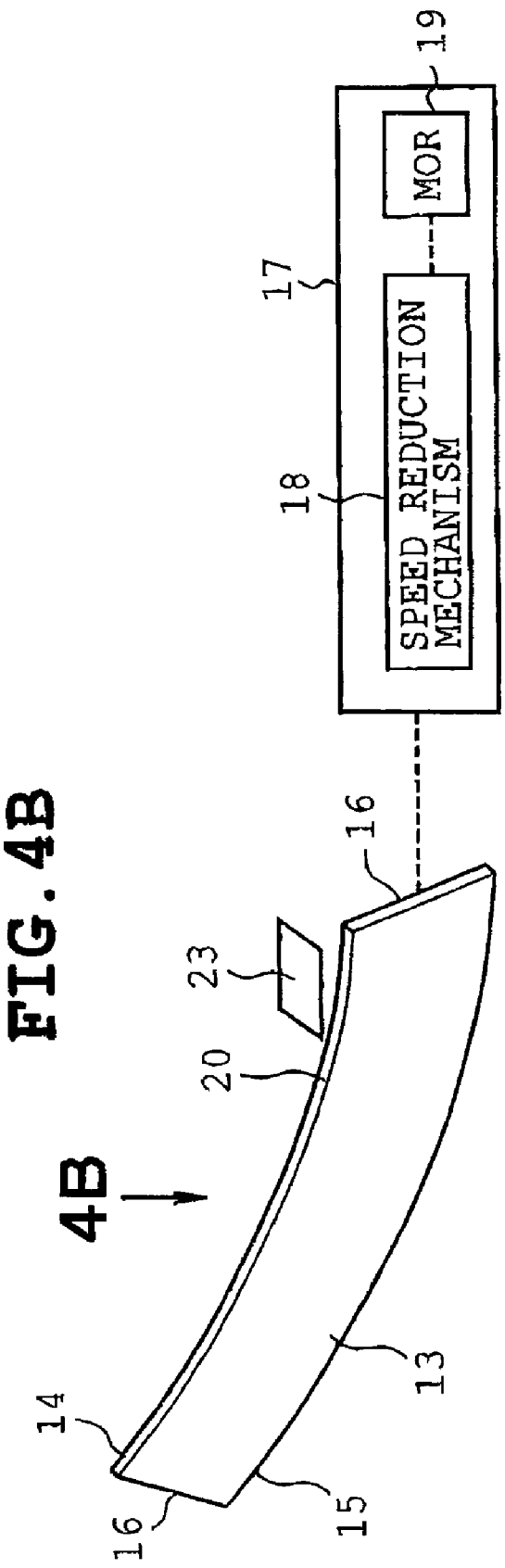
FIG. 4A is a perspective view of a leaf block.

Leaf drive mechanisms 17 serving as drive mechanisms are connected to the leaf blocks 13 respectively as shown in FIG. 4A. Each leaf drive mechanism 17 is moved circumferentially along a common circular locus ML about the center CP serving as the center of the locus. Each leaf drive mechanism 17 includes a speed reduction mechanism 18 and a leaf block motor 19 as shown in FIG. 4A. Each speed reduction mechanism 18 comprises a plurality of combined gears having diameters different from each other. Each speed reduction mechanism 18 further includes input and output shafts. Each leaf block motor 19 comprises a stepping motor and includes a rotational shaft connected to an input shaft of each speed reduction mechanism 18. The output shaft of each speed reduction mechanism 18 is connected to the corresponding leaf block 13. Each speed reduction mechanism 1B reduces torque of the leaf block motor 19 thereby to transmit the reduced torque to the leaf block 13. Each leaf block 13 of the first leaf block group 11 is operated so as to be moved in a departing direction in which each leaf block 13 of the first leaf block group 11 departs from the corresponding leaf block 13 of the second leaf block group 12 when the leaf block motor 19 is rotated in the normal direction as shown by arrow A in FIG. 5. When the leaf block motor 19 is reverse rotated as shown by arrow B in FIG. 5, each leaf block 13 of the first leaf block group 11 is operated so to be moved in an oncoming direction in which each leaf block 13 of the first leaf block group 11 comes close to the corresponding leaf block 13 of the second leaf block group 12. When each leaf block motor 19 is rotated in the normal direction as shown by arrow A in FIG. 5, the corresponding leaf block 13 of the second leaf block group 12 is operated so as to be moved in a departing direction in which each leaf block 13 of the second leaf block 12 departs from the corresponding leaf block 13 of the first leaf block group 11. When the leaf block motor 19 is reverse rotated as shown by arrow B in FIG. 5, the corresponding leaf block 13 of the second leaf block group 12 is operated so as to be moved in an oncoming direction in which each leaf block 13 of the second leaf block group 12 comes close to the corresponding leaf block 13 of the first leaf block group 11. Each leaf block motor 19 serves as a drive source.

Each leaf block 13 has a magnetic layer 20 formed on the entire arc-shaped face 14 which is a face along the movement direction of each leaf block 13, as shown in FIG. 4A. Each magnetic layer 20 is formed by applying a powdered magnetic material to the arc-shaped face 14 and has a plurality of magnetized portions 21 and another plurality of magnetized portions 22 both arranged alternately. The magnetized portions 21 are magnetized in the north pole and have the same circumferential dimension along the movement direction of the leaf blocks 13. The magnetized portions 22 are magnetized in the south pole and have the same circumferential dimension in the movement direction of the leaf blocks 13.

A plurality of magnetoresistive elements 23 (referred to as "MR sensor") are housed in the irradiation head 8 as shown in FIG. 4A. Each MR sensor 23 serves as a magnetic sensor and is disposed opposite the corresponding magnetic layer 20 of the leaf block 13 so as to be spaced from the magnetic layer 20 in the Y direction. Each MR sensor 23 is fixed inside the irradiation head 8 so as to be stationary in a noncontact state with respect to the magnetic layer 20 of the corresponding leaf block 13. When the leaf blocks 13 are moved in the departing direction or in the oncoming direction, the magnetized portions 21 and 22 alternately pass through a detection area of the MR sensor 23. The MR sensors 23 are disposed so that an element stripe is at right angles to a direction of magnetization of each MR sensor 23. When a resistance value of each MR sensor 23 varies with movement of the leaf blocks 13 in the departing or oncoming direction, each MR sensor 23 delivers pulse signals whose number depends upon an amount of movement of the corresponding leaf block 13. More specifically, every time each MR sensor 23 is moved in the departing or oncoming direction by a unit movement amount, the MR sensor 23 delivers one pulse signal. The multileaf collimator 10 is constructed and arranged as described above.

A radiation treatment computed tomography (CT) scanner 24 as shown in FIG. 2 scans a patient using radiation, obtaining image data of the patient based on the results of scanning. The CT scanner 24 transmits the obtained image data to a treatment planning device 25. The treatment planning device 25 is designed to work out radiation treatment based on the results of received image data and includes a treatment control circuit 26, a display 27 and an input device 28. The treatment control circuit 26 is mainly composed of a microcomputer and receives image data transmitted from the CT scanner and displays the received image data on the display 27. The display 27 comprises a cathode ray tube (CRT). When having visually recognized the contents displayed on the display 27, the operator determines the location of an affected part and an exposure field of X rays. The input device 28 includes a rectangular region of interest (ROI), a polyline, a cross ROY, a keyboard and a track board. The input device 28 serves as an operating member which is operated by the operator so that the results of determination regarding the location of the affected part of the patient and exposure field of X rays are entered. The treatment control circuit 26 recognizes results of entry of the location of the affected part and exposure field of X rays, based on the operation contents by the input device 28.

A main control circuit 30 is connected via an Interface circuit 29 to the treatment control circuit 26 as shown in FIG. 2. The treatment control circuit 26 transmits the results of recognition regarding the location of the affected part and the exposure field of X rays. The main control circuit 30 is mainly composed of a microcomputer having a central processing unit (CPU), a random access memory (RAM) and a read only memory (ROM). The main control circuit 30 sets target location data of the treatment table 2 in the X direction, target location data of the treatment table 2 in the Y direction and target location data of the mount 5 in the R direction. These target location data are set so that X rays are irradiated from the outlet of the irradiation head 8 onto a part according to the received results of the location of affected part.

The main control circuit 30 sets a movement amount Na of each of a plurality of (28, for example) of leaf blocks 13, based on the results of received exposure field of X rays. The movement amount Na of each leaf block 13 is set so that a space having a target configuration according to the results of received exposure field is defined between the first and second leaf block groups 11 and 12. For this purpose, the leaf blocks 13 are assigned with identification numbers 1 to 28. The movement amount Na is set for every one of the identification numbers 1 to 28. Each movement amount Na defines an amount of movement of the corresponding leaf block 13 in the departing direction A on the basis of an origin position Z0.

Figure 5:
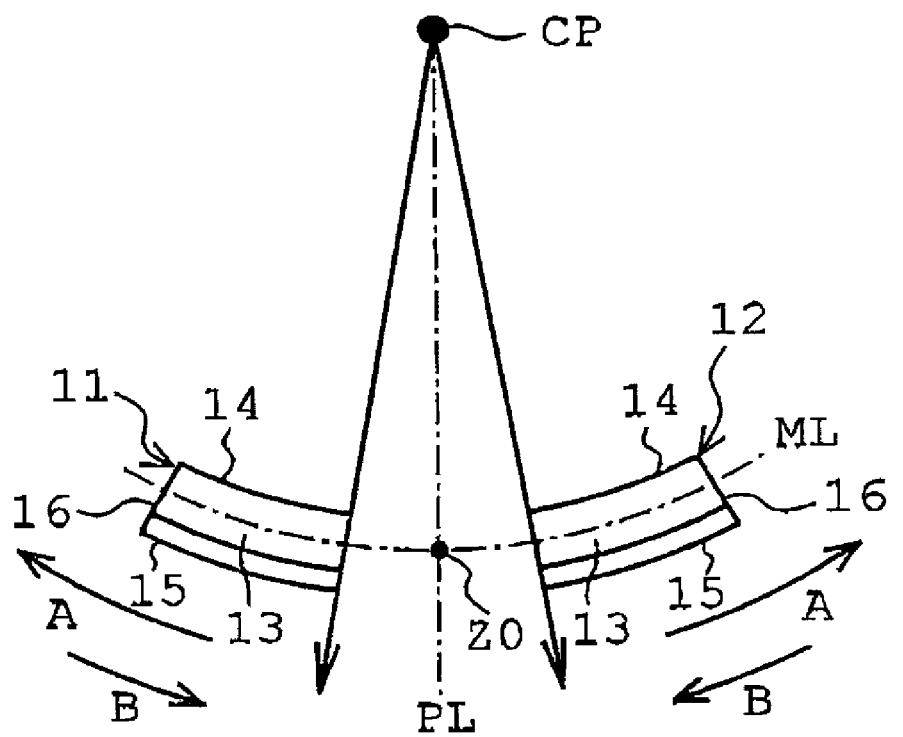
FIG. 5 shows the leaf block as viewed from a direction perpendicular to another direction in which the X-ray is irradiated.
Figure 5:
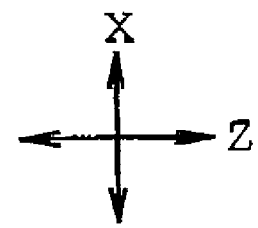

The origin position Z0 is set on a plane PL which passes the center point CP and vertical in the Y direction as shown in FIG. 5. Each movement amount Na is set as the number of pulse signals delivered by the MR sensor 23.

To the main control circuit 30 are connected a mount control circuit 31, an irradiation control circuit 32, a collimator control circuit 33 and a treatment table control circuit 34 as shown in FIG. 2. The main control circuit 30 transmits to the mount control circuit 31 a result of setting of data of target position of the mount 5 in the R direction. The main control circuit 30 also delivers to the collimator control circuit 33 a result of setting of data of movement amount Na of each leaf block 13. The main control circuit 30 further delivers to the treatment table control circuit 34 a result of setting of data of a target position of the treatment table 2 in the X direction. Each of the circuits 31 to 34 comprises as a main component a microcomputer having a CPU, a ROM and a RAM.

The irradiation control circuit 32 controls the X-radiation generator 9. The X-radiation generator 9 starts irradiating radiation based on an operation start signal delivered by the irradiation control circuit 32. The X-radiation generator 9 stops irradiation of X-radiation when receiving an operation stop signal from the irradiation control circuit 32. The mount control circuit 31 controls an amount of rotation of the Redirection motor based on a result of receipt of data of target position in the R direction, so that the mount 5 is operated so as to be moved to the target position in the R direction according to the result of receipt of data of target position in the R direction. The treatment table control circuit 34 controls an amount of rotation of the X-direction motor according to a result of receipt of data of target position in the X direction. The treatment table control circuit 34 also controls an amount of rotation of the Y-direction motor according to a result of receipt of data of target position in the Y direction. Thus, the treatment table 2 is moved to the target position according to the results of receipt of data of target positions in the X and Y directions. As a result, the position of X-radiation is moved to a position according to data of target positions in the X and Y directions, and the mount 5 is moved to a position according to the received data of target position in the R direction, whereupon the position of X-radiation is set to the entered position of the affected part.

The collimator control circuit 33 serves as a control device. The leaf block motors 19 of a plurality of leaf drive mechanisms 17 are connected via respective motor drive circuits 35 to the collimator control circuit 33 as shown in FIG. 2. Each motor drive circuit 35 applies normal rotation pulse signals and reverse rotation pulse signals to the corresponding leaf block motor 19. The collimator control circuit 33 thus controls each of the motor drive circuits 35 so that the leaf blocks 13 are individually operated so as to be moved in the departing and oncoming directions. The MR sensors 23 are connected to the collimator control circuit 33 so that the collimator control circuit 33 controls an amount of rotation of each leaf block motor 19 based on the pulse signals delivered by the MR sensor 23. As a result, each leaf block 13 is moved to a position according to the set movement amount Na, whereupon a space having a target configuration according to the received exposure field is defined between the first and second leaf block groups 11 and 12.

Figure 6:
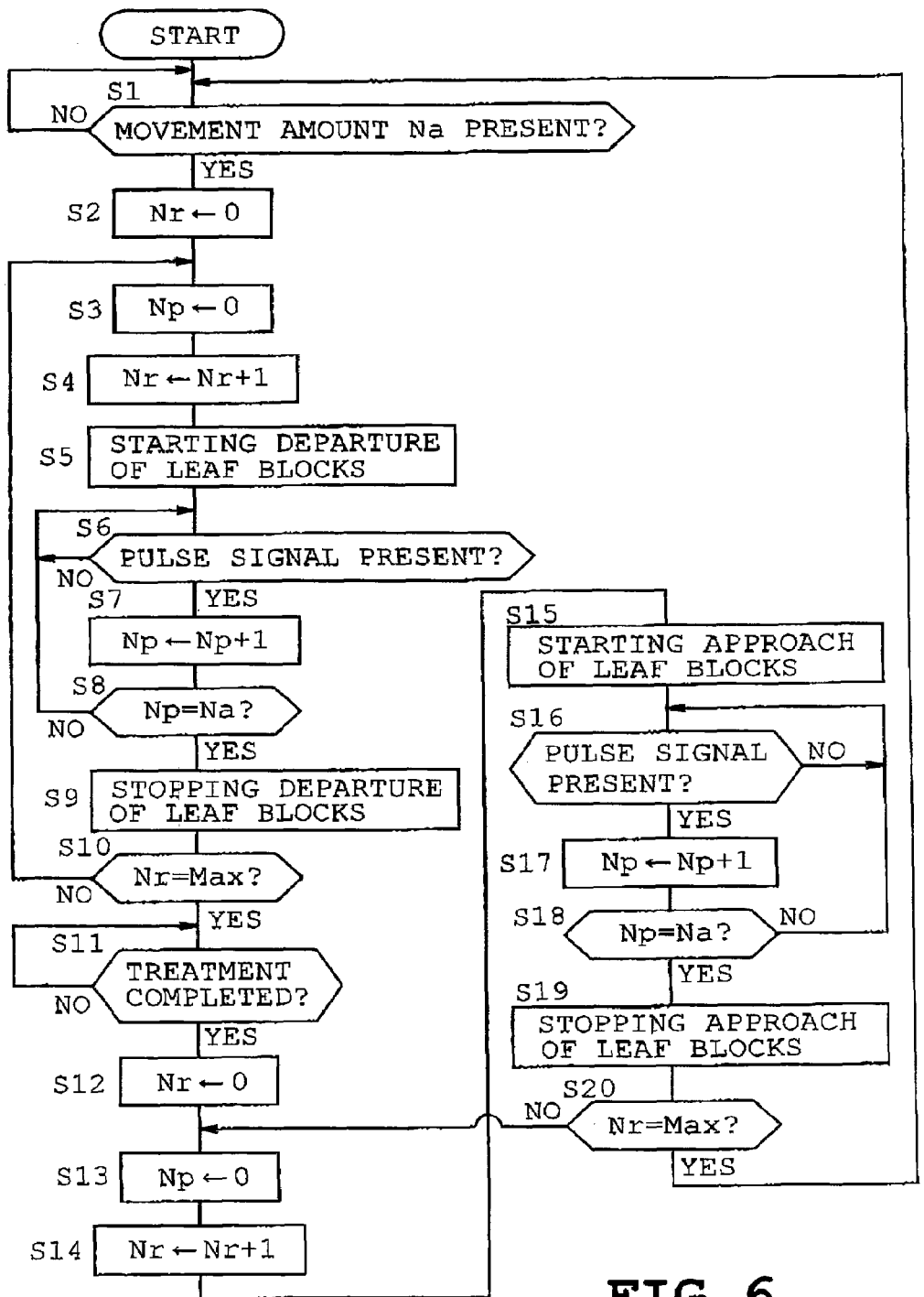
FIG. 6 is a flowchart showing the control contents of a collimator control circuit.

FIG. 6 shows a control program previously stored on a ROM of the collimator control circuit 33. The collimator control circuit 33 includes a CPU which controls each leaf block motor 19 based on the control program of FIG. 6 so that a space having a target configuration according to the received exposure field is defined between the first and second leaf block groups 11 and 12.

The control program will be described with reference to FIG. 6. When receiving each set movement amount Na at step S1 in FIG. 6r the CPU of the collimator control circuit 33 advances to step S2 to reset a leaf block counter Nr of the RAM to 0. The leaf block counter Nr is provided for specifying a leaf block 13 whose position is to be controlled. When having reset the leaf block counter Nr at step S2, the CPU advances to step S3 to reset a pulse counter Np of the RAM to 0. The pulse counter Np is provided for counting the number of pulse signals delivered by each MR sensor 23. When having reset the pulse counter Np at step S3, the CPU advances to step S4 to add "1" to the leaf block counter Nr.

When having added "1" to the leaf block counter Nr at step S4, the CPU advances to step S5 to start operation of the leaf block motor 19 in the forward direction according to the addition to the leaf block counter Nr. As a result, the leaf block 13 according to the addition to the leaf block counter Nr is moved in the departing direction A. Step S5 serves as a movement starting unit and a movement starting step. When the leaf block 13 according to the addition to the leaf block counter Nr has been moved in the departing direction A, the CPU advances to step S6 to determine whether one pulse signal has been delivered by the MR sensor 23 according to the addition to the leaf block counter Nr When determining at step S6 that one pulse signal has been delivered by the MR sensor 23, the CPU advances to step S7 to add "1" to the pulse counter Np. Step S7 serves as a movement amount detection unit and a movement amount detection step.

When having added to the pulse counter Np at step S7, the CPU advances to step S8 to compare the result of addition to the pulse counter Np with the movement amount Na set according to the addition to the leaf block counter Nr. Step S8 serves as a determination unit and a determination step. For example, when the leaf block 13 set according to the addition to the leaf block counter Nr is moved by the set movement amount Na in the departing direction A, the CPU determines at step S8 that Np=Na and further advances to step S9 to stop the leaf block motor 19 according to the addition to the leaf block counter Nr. Step S9 serves as a movement stopping unit and a movement stopping step. The CPU advances to step S10 when having stopped the leaf block motor according to the addition to the leaf block counter Nr at step S9. At step S10, the CPU compares the result of addition to the counter Nr with the maximum value (Max(=28)) previously stored on the ROM. The CPU returns to step S3 when having determined that Nr<28.

When having returned to step S3, the CPU resets the pulse counter Np to 0. The CPU then advances to step S4 to add "1" to the leaf block counter Nr, further advancing to step S5 to start moving in the departing direction A the leaf block 13 according to the result of addition to the leaf block counter Nr. The CPU then repeats steps S6 to S8 so that the leaf block 13 according to the result of addition to the leaf block counter Nr is moved in the departing direction A by the set movement amount Na.

When all the leaf blocks 13 have been moved by the movement amount Na in the departing direction A, the CPU determines at step S10 that Nr=Max. In this case, the CPU advances to step S11 to determine whether a treatment completion signal is present. The main control circuit 30 transmits the treatment completion signal to the collimator control circuit 33 when the process of applying X rays has been completed. The CPU advances to step S12 when having determined at step S11 that the treatment completion signal is present. At step S12, the CPU resets the leaf block counter Nr to 0. The CPU then advances to step S13 to reset the pulse counter Np to 0 and further to step S14 to add "1" to the leaf block counter Nr. The CPU then advances to step S15 to start operation in the reverse direction of the leaf block motor 19 specified based on the result of addition to the leaf block counter Nr. Based on the start of operation of the leaf block motor 19, the CPU starts movement in the oncoming direction B of the leaf block 13 specified based on the result of addition to the leaf block counter Nr.

When having started the movement of the leaf block 13 in the reverse direction at step S15, the CPU then advances to step S1 to determine whether one pulse has been delivered by the MR sensor 23 specified based on the result of addition to the leaf block counter Nr. When determining that one pulse has been delivered by the MR sensor 23, the CPU advances to step S17 to add "1" to the pulse counter Np. When having added "1" to the leaf block counter Np at step S17, the CPU advances to step S18 to compare the result of addition to the pulse counter Np with the result of setting of movement amount Na according to the result of addition to the leaf block counter Nr. For example, when the leaf block 13 specified based on the result of addition to the leaf block counter Nr has been returned to the origin position Z0, the CPU determines at step S18 that Np=Na, advancing to step S19. The CPU stops the operation of the leaf block motor 19 specified based on the result of addition to the leaf block counter Nr at step S19. The CPU then advances to step S20 to compare the result of addition to the leaf block counter Nr with the maximum value (Max). When determining that Nr<Max, the CPU returns to step S13. When having returned to step S13, the CPU resets the pulse counter to "0." The CPU then advances to step S14 to add "1" to the leaf block counter Nr and to start movement in the oncoming direction B of the lead block 13 specified based on the leaf block counter Nr. The CPU then repeats steps S16 to S18 so that the leaf block 13 specified based on the leaf block counter Nr is operated so as to be moved to the origin position. When the process of returning to the origin position has been applied to all the leaf blocks 13, the CPU determines at step S20 that Nr=Max, returning to step S1.

According to the foregoing embodiment, the magnetic layer 20 is provided on the arc-shaped face 15 of each leaf block 13 extending in the movement direction of each leaf block 13. The magnetic layer 20 has the magnetized portions 21 magnetized in the north pole and the other magnetized portions 22 magnetized in south pole. The MR sensors 23 are disposed in the noncontact state with respect to the respective magnetic layers 20 so as to be stationary. Each leaf drive mechanism 17 is driven based on the output signal of the MR sensor 23 so that each leaf block 13 is operated so as to be moved to the target position in the noncontact manner. Consequently, the space between the first and second leaf block groups 11 and 12 can accurately be set to the target configuration according to the result of input of the exposure field without adverse affection due to variations in the electrical resistance value.

In the foregoing embodiment, the magnetic layer 20 having alternately arranged magnetized portions 21 and 22 may be formed on a part of the arc-shaped face of each leaf block 13.

Figure 7:
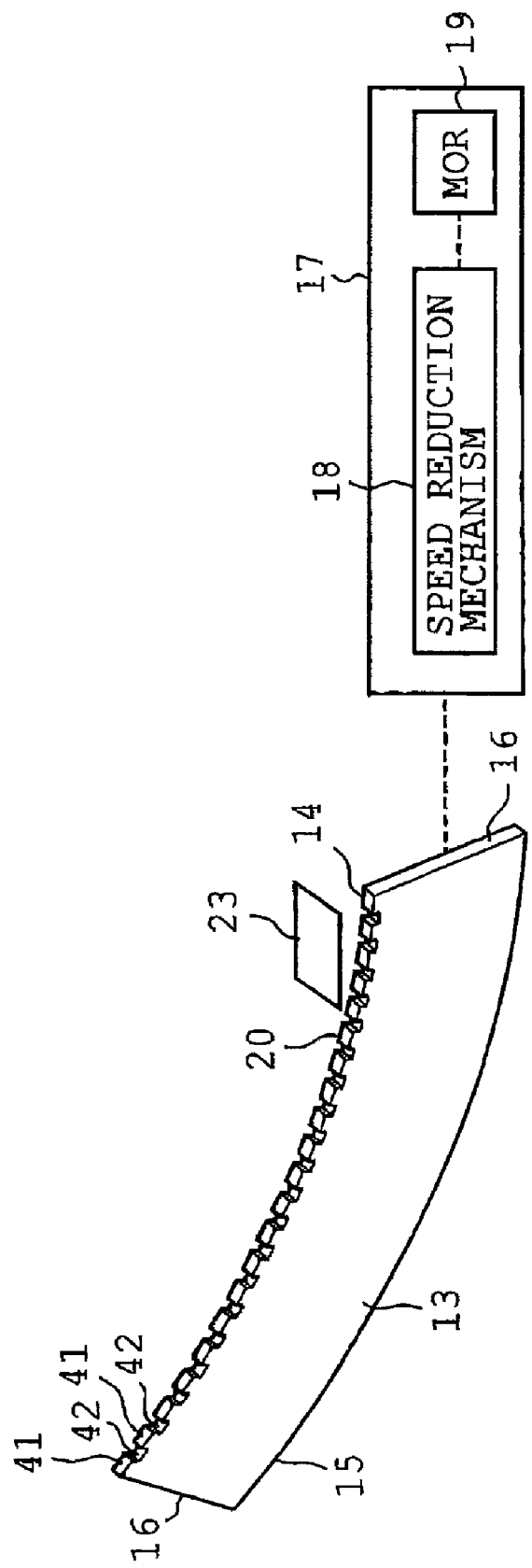
FIG. 7 is a view similar to FIG. 4A, showing a second embodiment of the invention.

FIG. 7 illustrates a second embodiment of the invention. Each leaf block 13 has a plurality of convex portions 41 and a plurality of concave portions 42 alternately formed on the overall arc-shaped face 14 as shown in FIG. 7. The convex portions 41 are circumferentially arranged at regular intervals and have the same circumferential dimension. The concave portions 42 are arranged circumferentially at regular intervals and have the same circumferential dimension as the concave portions 41.

The magnetic layers 20 are formed on the leaf blocks 13 so as to be located on the entire arc-shaped faces 14 respectively.

Each magnetic layer 20 is formed by applying a powdered magnetic material to the arc-shaped face 14 from over the convex and concave portions 41 and 42. The magnetized portion 21 magnetized in the north pole and the magnetized portion 22 magnetized in the south pole are located on the surface of each convex portion 41. Also, the magnetized portion 21 magnetized in the north pole and the magnetized portion 22 magnetized in the south pole are located on the surface of each concave portion 42. The MR sensors 23 are disposed above the magnetic layers 20 in the noncontact state with respect to the respective magnetic layers 20 so as to be stationary. The collimator control circuit 33 controls each of the plural leaf block motors 19 based on the control program as shown in FIG. 6 so that a space having a target configuration according to the results of delivered exposure field is defined between the first and second leaf block groups 11 and 12.

According to the second embodiment, the arc-shaped faces 14 of the plural leaf blocks 13 have the convex and concave portions 41 and 42 formed alternately along the direction of movement of the leaf blocks 13. The magnetic layer 20 is formed on the arc-shaped face 14 of each leaf block 13 so as to be applied from over the convex and concave portions 41 and 42. Accordingly, when each leaf block 13 is moved in the departing or oncoming direction, the convex and concave portions 41 and 42 pass through a detection area of the MR sensor alternately. Consequently, each MR sensor 23 can be subjected to high and low magnetic fields from the leaf blocks 13 alternately.

In the second embodiment, the convex and concave portions 41 and 42 both having magnetic layers 20 are alternately formed on a part of the arc-shaped face 14 of each leaf block 13. The magnetized portions 21 and 22 may alternately be formed on portions of the magnetic layer 20 corresponding to the convex portions 41, and the magnetized portions 21 and 22 may alternately be formed on portions of the magnetic layer 20 corresponding to the concave portions 42.

In the second embodiment, only the magnetized portions 21 magnetized in the north pole may be formed on portions of the magnetic layer 20 corresponding to the convex portions 41, and only the magnetized portions 22 magnetized in the south pole may be formed on portions of the magnetic layer 20 corresponding to the concave portions 42.

In the second embodiment, only the magnetized portions 22 magnetized in the south pole may be formed on portions of the magnetic layer 20 corresponding to the convex portions 41, and only the magnetized portions 21 magnetized in the north pole may be formed on portions of the magnetic layer 20 corresponding to the concave portions 42.

In each of the first and second embodiments, a rubber-like magnetic material may be affixed to the arc-shaped face 15 of each leaf block 13 so that the magnetic layer 20 is formed.

In each of the first and second embodiments, each MR sensor 23 may be disposed in the noncontact state so as to be stationary below the magnetic layer 20 which is provided on the arc-shaped face 15 of each leaf block 13 and has the magnetized portions 21 and 22.

Hall elements may be used instead of the MR sensors 23 in each of the first and second embodiments. Additionally, the collimator control circuit 33 may be arranged to control the leaf block motor 19 so that a part or overall leaf blocks 13 are moved in a batch.

The foregoing description and drawings are merely illustrative of the principles of the present invention and are not to be construed in a limiting sense. Various changes and modifications will become apparent to those of ordinary skill in the art. All such changes and modifications are seen to fall within the scope of the invention as defined by the appended claims.

What is claimed is:

1. A multileaf collimator comprising:
    a first leaf block group including a plurality of leaf blocks arranged in a direction;
    a second leaf block group including a plurality of leaf blocks arranged in the same direction as the first leaf block group, the leaf blocks of the second leaf block group being opposed to the leaf blocks of the first leaf block group in a direction orthogonal to the direction in which the leaf blocks of the first leaf block group are arranged;
    a plurality of drive mechanisms provided on the respective leaf blocks of the first and second leaf block groups, the drive mechanisms moving the leaf blocks of the first or second leaf block group in an oncoming direction in which the leaf blocks of the first or second leaf block group come close to the leaf blocks of the second or first leaf block or in a departing direction in which the leaf blocks of the first or second leaf block group depart from the leaf blocks of the second or first leaf block group;
    a plurality of magnetic layers which are provided on the respective leaf blocks of the first and second leaf block groups so as to be positioned on faces of the leaf blocks along a moving direction of the leaf blocks, each of the magnetic layers having a first magnetized part which is magnetized in a north pole and a second magnetized part which is magnetized in a south pole;
    a plurality of magnetic sensors which are provided on the respective leaf blocks of the first and second leaf block groups, the magnetic sensors being stationary in a non-contact state with respect to the respective leaf blocks, the magnetic sensors varying output signals when the respective leaf blocks are moved in the oncoming direction or the departing direction; and
    a control device which controls the drive mechanisms according to the output signals delivered by the respective magnetic sensors so that a space defined between the leaf blocks of the first and second leaf blocks is adjusted into a target configuration.

2. The multileaf collimator according to claim 1, wherein the first and second magnetized parts magnetized in the north and south poles respectively are disposed alternately in a direction of movement of the leaf blocks.

3. The multileaf collimator according to claim 1, wherein each leaf block of the first and second leaf block groups has a face extending in a direction of movement of the leaf blocks, the face having concave and convex portions formed alternately, and each magnetic layer is disposed on the face of each leaf block so as to cover the concave and convex portions.

4. A control device for a multileaf collimator which includes a first leaf block group including a plurality of leaf blocks arranged in a direction, a second leaf block group including a plurality of leaf blocks arranged in a same direction as the first leaf block group, the leaf blocks of the second leaf block group being opposed to the leaf blocks of the first leaf block group in a direction orthogonal to the direction in which the leaf blocks of the first leaf block group are arranged, a plurality of drive mechanisms provided on the respective leaf blocks of the first and second leaf block groups, the drive mechanisms moving the leaf blocks of the first or second leaf block group in an oncoming direction in which the leaf blocks of the first or second leaf block group come close to the leaf blocks of the second or first leaf block or in a departing direction in which the leaf blocks of the first or second leaf block group depart from the leaf blocks of the second or first leaf block group, a plurality of magnetic layers which are provided on the respective leaf blocks of the first and second leaf block groups so as to be positioned on faces of the leaf blocks along a moving direction of the leaf blocks, each of the magnetic layers having a first magnetized part which is magnetized in a north pole and a second magnetized part which is magnetized in a south pole, a plurality of magnetic sensors which are provided on the respective leaf blocks of the first and second leaf block groups, the magnetic sensors being stationary in a noncontact state with respect to the respective leaf blocks, the magnetic sensors varying output signals when the respective leaf blocks are moved in the oncoming direction or the departing direction, and a control device which controls the drive mechanisms according to the output signals delivered by the respective magnetic sensors so that a space defined between the leaf blocks of the first and second leaf blocks is adjusted into a target configuration, the control device comprising:

a movement starting unit which carries out a movement starting process in which movement of the leaf blocks in the departing direction is processed with a predetermined origin position serving as a starting point when an operation of the drive mechanism is started, the movement starting unit carrying out the movement starting process for everyone of the leaf blocks of the first and second leaf block groups;

a movement amount detection unit which carries out a movement amount detection process in which an amount of movement of each leaf block in the departing direction is detected on the basis of the origin position based on a variation in an output signal delivered by the magnetic sensor, the movement amount detection unit carrying out the movement amount detecting process for every one of the leaf blocks of the first and second leaf block groups;

a determination unit which carries out a determining process which determines whether a result of detection by the movement amount detection unit has reached a target movement amount, the determination unit carrying out the determining process for every one of the leaf blocks of the first and second leaf block groups; and a movement stopping unit which carries out a movement stopping process in which the movement stopping unit stops an operation of the drive mechanism when the determination unit has determined that a result of detection by the movement amount detection unit has reached the target movement amount, the movement stopping unit carrying out the movement stopping process for every one of the leaf blocks of the first and second leaf block groups.

5. A method of controlling a multileaf collimator which includes a first leaf block group including a plurality of leaf blocks arranged in a direction, a second leaf block group including a plurality of leaf blocks arranged in the same direction as the first leaf block group, the leaf blocks of the second leaf block group being opposed to the leaf blocks of the first leaf block group in a direction orthogonal to the direction in which the leaf blocks of the first leaf block group are arranged, a plurality of drive mechanisms provided on the respective leaf blocks of the first and second leaf block groups, the drive mechanisms moving the leaf blocks of the first or second leaf block group in an oncoming direction in which the leaf blocks of the first or second leaf block group come close to the leaf blocks of the second or first leaf block or in a departing direction in which the leaf blocks of the first or second leaf block group depart from the leaf blocks of the second or first leaf block group, a plurality of magnetic layers which are provided on the respective leaf blocks of the first and second leaf block groups so as to be positioned on faces of the leaf blocks along a moving direction of the leaf blocks, each of the magnetic layers having a first magnetized part which is magnetized in a north pole and a second magnetized part which is magnetized in a south pole, a plurality of magnetic sensors which are provided on the respective leaf blocks of the first and second leaf block groups, the magnetic sensors being stationary in a noncontact state with respect to the respective leaf blocks, the magnetic sensors varying output signals when the respective leaf blocks are moved in the oncoming direction or the departing direction, and a control device which controls the drive mechanisms according to the output signals delivered by the respective magnetic sensors so that a space defined between the leaf blocks of the first and second leaf blocks is adjusted into a target configuration, the method comprising:

starting movement of the leaf blocks in the departing direction with a predetermined origin position serving as a starting point when an operation of the drive mechanism is started, the movement starting step being carried out for every one of the leaf blocks of the first and second leaf block groups;

detecting an amount of movement of each leaf block in the departing direction on the basis of the origin position based on a variation in an output signal delivered by the magnetic sensor, the movement amount detecting step being carried out for every one of the leaf blocks of the first and second leaf block groups;

determining whether a result of detection by the movement amount detection unit has reached a target movement amount, the determining step being carried out for every one of the leaf blocks of the first and second leaf block groups; and stopping an operation of the drive mechanism when the determination unit has determined that a result of detection by the movement amount detection unit has reached the target movement amount, the movement stopping step being carried out for every one of the leaf blocks of the first and second leaf block groups.

6. A radiation treatment machine comprising:
a treatment table on which a patient is put;
a radiation generator which applies medical treatment radiation to an affected part of the patient on the treatment table; and
a multileaf collimator which adjusts the radiation applied to the patient according to a shape of the affected part, the multileaf collimator comprising:

a first leaf block group including a plurality of leaf blocks arranged in a direction;

a second leaf block group including a plurality of leaf blocks arranged in the same direction as the first leaf block group, the leaf blocks of the second leaf block group being opposed to the leaf blocks of the first leaf block group in a direction orthogonal to the direction in which the leaf blocks of the first leaf block group are arranged;

a plurality of drive mechanisms provided on the respective leaf blocks of the first and second leaf block groups, the drive mechanisms moving the leaf blocks of the first or second leaf block group in an oncoming direction in which the leaf blocks of the first or second leaf block group come close to the leaf blocks of the second or first leaf block or in a departing direction in which the leaf blocks of the first or second leaf block group depart from the leaf blocks of the second or first leaf block group;

a plurality of magnetic layers which are provided on the respective leaf blocks of the first and second leaf block groups so as to be positioned on faces of the leaf blocks along a moving direction of the leaf blocks, each of the magnetic layers having a first magnetized part which is magnetized in a north pole and a second magnetized part which is magnetized in a south pole;

a plurality of magnetic sensors which are provided on the respective leaf blocks of the first and second leaf block groups, the magnetic sensors being stationary in a noncontact state with respect to the respective leaf blocks, the magnetic sensors varying output signals when the respective leaf blocks are moved in the oncoming direction or the departing direction; and a control device which controls the drive mechanisms according to the output signals delivered by the respective magnetic sensors so that a space defined between the leaf blocks of the first and second leaf blocks is adjusted into a target configuration.

7. The radiation treatment machine according to claim 6, wherein the first and second magnetized parts magnetized in the north and south poles respectively are disposed alternately in a direction of movement of the leaf blocks.

8. The radiation treatment machine according to claim 6, wherein each leaf block of the first and second leaf block groups has a face extending in a direction of movement of the leaf blocks, the face having concave and convex portions formed alternately, and each magnetic layer is disposed on the face of each leaf block so as to cover the concave and convex portions.

* * * * *

UNITED STATES PATENT AND TRADEMARK OFFICE
CERTIFICATE OF CORRECTION

PATENT NO. : 7,564,951 B2
APPLICATION NO. : 12/053879
DATED : July 21, 2009
INVENTOR(S) : Yukihisa Hasegawa et al.

It is certified that error appears in the above-identified patent and that said Letters Patent is hereby corrected as shown below:

Column 4, line 24, please replace "1b" with -- 18 --.

Column 6, line 24-25, please replace "Redirection" with -- R-direction --.

Column 7, line 3, please replace "6r" with -- 6, --.

Column 8, line 10, please replace "S1" with -- S16 --.

Signed and Sealed this

Eighth Day of December, 2009

David J. Kappos
*Director of the United States Patent and Trademark Office*